US005309640A

United States Patent [19]

Caron

[11] Patent Number: 5,309,640

[45] Date of Patent: May 10, 1994

[54] INSTRUMENT FOR CUTTING HAIR AND SIMULTANEOUSLY CAUTERIZE THE CUT HAIR ENDS

[75] Inventor: Giovanni Caron, Varese, Italy

[73] Assignee: S.E.R.P.A.T. s.r.l, Varese, Italy

[21] Appl. No.: 961,687

[22] PCT Filed: Jul. 8, 1991

[86] PCT No.: PCT/IT91/00058

§ 371 Date: Feb. 3, 1993

§ 102(e) Date: Feb. 3, 1993

[87] PCT Pub. No.: WO92/00688

PCT Pub. Date: Jan. 23, 1992

[30] Foreign Application Priority Data

Jul. 10, 1990 [IT] Italy .............................. 83625 A/90

[51] Int. Cl.[5] .............................................. A61B 17/38

[52] U.S. Cl. ........................................ 30/140; 30/254; 219/227

[58] Field of Search ............................ 30/140; 606/28; 219/221, 230, 235, 236, 227

[56] References Cited

U.S. PATENT DOCUMENTS

| | | | |
|---|---|---|---|
| 1,083,386 | 1/1914 | Chapman | 30/140 |
| 3,892,024 | 7/1975 | Van Zyl | 30/140 |
| 4,516,574 | 5/1985 | Hewes, Jr. | 30/140 |
| 4,587,968 | 5/1986 | Price | 30/140 |
| 5,046,251 | 9/1991 | Scott | 30/140 |

FOREIGN PATENT DOCUMENTS

| | | | |
|---|---|---|---|
| 1502767 | 11/1967 | France | 30/140 |
| 2407797 | 6/1979 | France . | |
| 2532878 | 3/1984 | France . | |
| 2612381 | 9/1988 | France . | |

*Primary Examiner*—Richard K. Seidel
*Assistant Examiner*—Hwei-Siu Payer
*Attorney, Agent, or Firm*—Pollock, Vande Sande & Priddy

[57] ABSTRACT

Scissors for cutting hair while simultaneously cauterizing the cut hair ends having an electrically heated blade. Heating resistance is set in a recess of a blade-holder portion for each knife of the scissors. A heat sensor is also included in at least one of the knives.

4 Claims, 4 Drawing Sheets

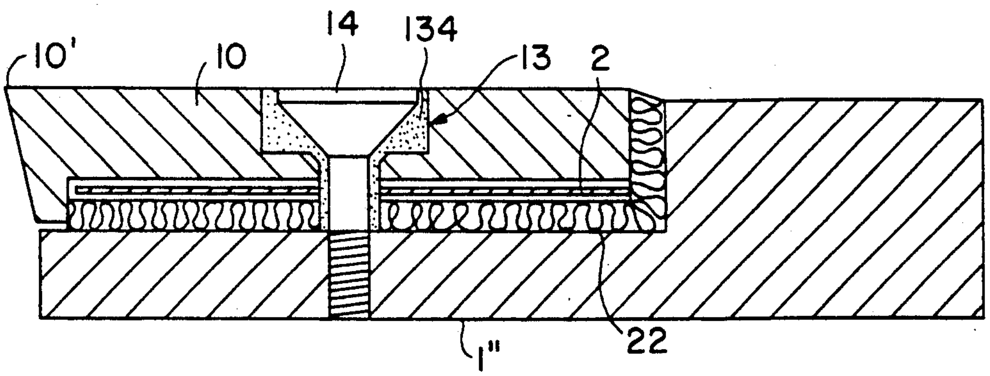
FIG. 2
FIG. 3
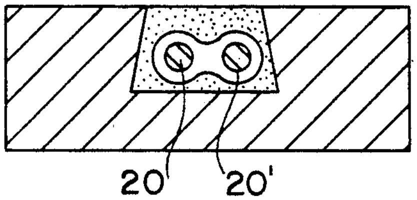
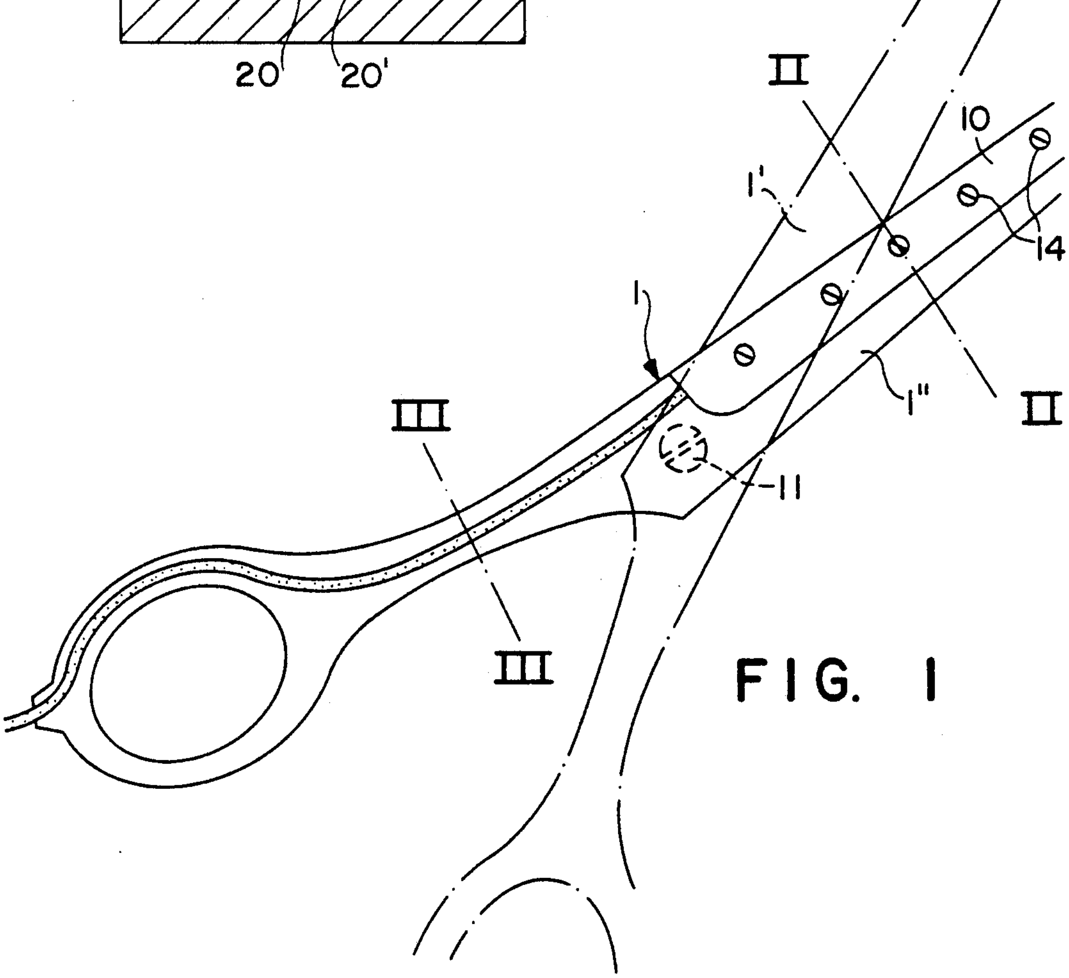
FIG. 1

FIG. 5
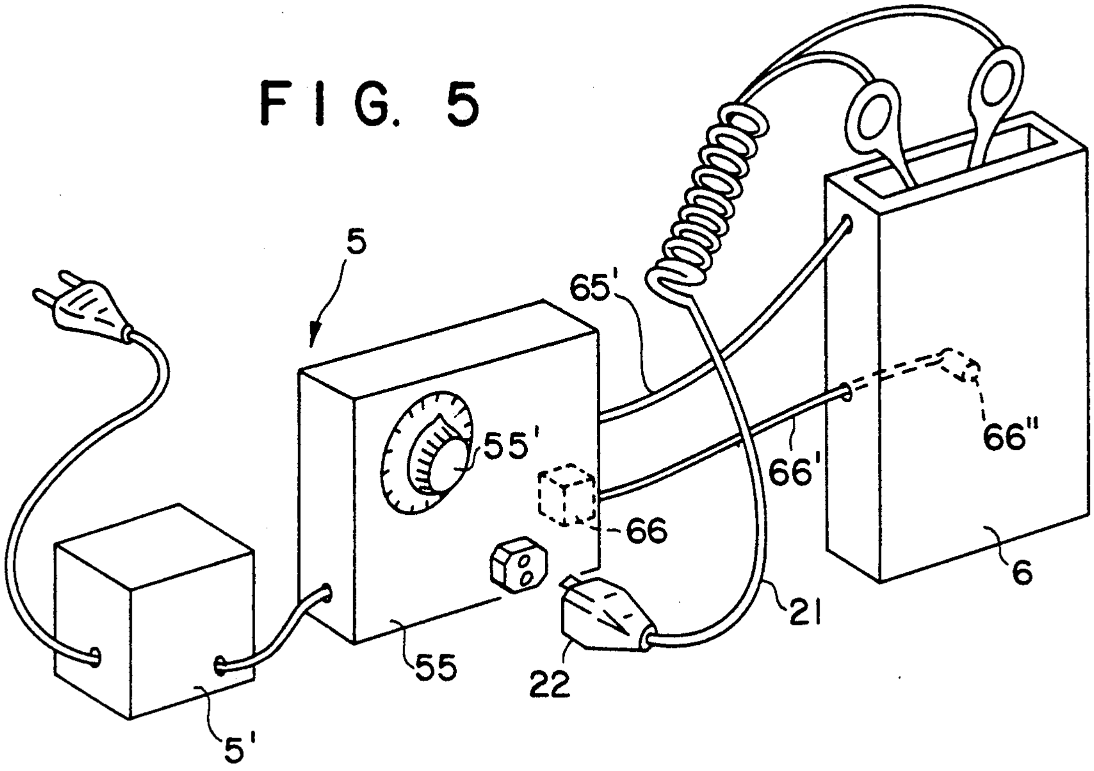
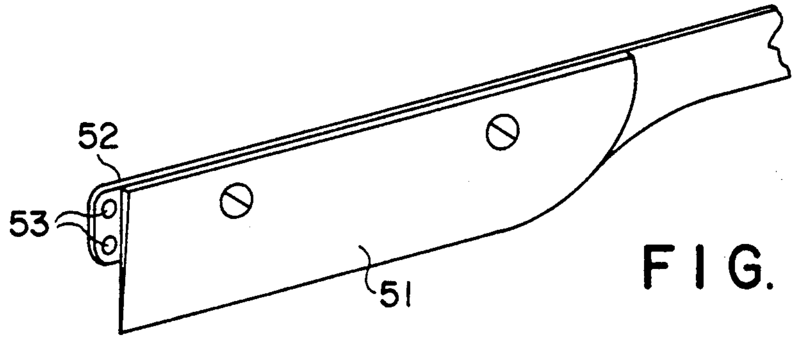
FIG. 9
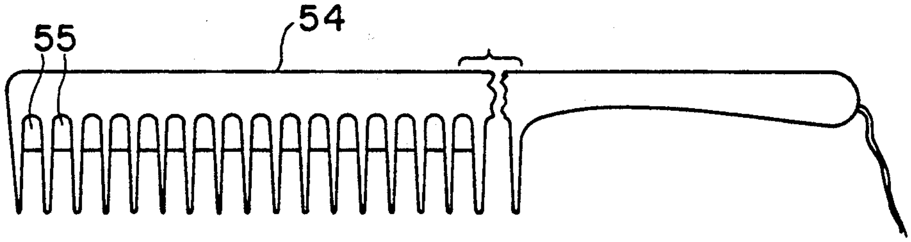
FIG. 10

INSTRUMENT FOR CUTTING HAIR AND SIMULTANEOUSLY CAUTERIZE THE CUT HAIR ENDS

TECHNICAL FIELD

The present invention relates to an instrument for cutting hair, as one of the instruments which are normally used by hairdressers, capable of simultaneously cauterized the cut hair ends.

BACKGROUND ART

Until now there has not been any relation among the functions performed by means of conventional scissors by hairdressers and other conservatory acts which are performed on hair by means of other specialized instruments, in particular for preventing the growth of bifurcated hair ends, which is a frequent but not exclusive concern of women keeping relatively long hair. It has been heretofore a common practice of hairdressers to cure the tendency of hair to bifuracate by flame treating the hair, using a candle or a special torch. These treatments are time consuming and unpleasant to both the customer-patient and the operator, moreover the risks of inadvertently overdamaging the hair or to accidentally cause more serious damages is attendant.

SUMMARY OF INVENTION

A main objective of the present invention is to provide an instrument for simultaneously cauterizing the cut hair ends while cutting hair in a safe and effective manner, while causing the least discomfort to the customer.

These objectives and other advantages are achieved by means of the instrument object of the present invention which consists in a hair cutting instrument having, under this aspect a substantially common configuration, while the cutters or the cutter thereof is electrically heated to a temperature comprised in the range of 150° C. and 300° C. for cauterizing the hair being cut by the blade.

It has been found that hair cut with a blade held at such a high temperature shows a markedly reduced tendency to bifurcate upon growth and the hair comparatively appears to benefit overall from the high temperature cut treatment, by developing an improved glossy appearance and an overall reinvigoration. These positive effects may be attributed to the simultaneous cauterization of the cut produced in the hair which prevents a tendency of the hair to desquamate or to "loosen" at the freshly produced cut which may originate degenerative processes such as the bifurcation of the hair and the like. In this respect, the high temperature cut produced by the instrument of the present invention may be seen as providing a positive aseptic "sealing" of the cut which prevents degenerative effects after the cutting.

According to a first embodiment of the invention, the instrument is a pair of scissors, at least a blade or preferably both blades of which are heated. However other embodiments may be in the form of single blade hair cutting instruments such as a razor and also of a comb-razor, as often used by hairdressers in place of scissors for performing special hairdressings. The cutter or the cutters, as the case may be, are preferably heated by electrical heaters which are preferably set into an especially designed blade holder portion of the instrument in order to generate the required heat as close as possible to the cutting edge. Most preferably the instrument has heater elements incorporated therein and connected to a low voltage power supply through an insulated cable and most preferably the instrument is also provided with a thermocouple set in proximity of the heated blade and which is connectable through the same (multiconductor) insulated cable to a temperature control unit in order to maintain the cutting blade or the cutting blades to a presettable constant temperature during the utilization of the hair cutting instrument. The temperature control-power supply unit may be combined in a wheeled caddie and be provided with a panel including all the control and temperature preselection switches and with a display for monitoring the correct temperature to which the cutters are heated.

The different aspect and advantages of the haircut instrument of the present invention will be more easily appreciated through the following detailed description of several embodiments and reference to the attached drawings.

BRIEF DESCRIPTION OF DRAWINGS

FIG. 1 is a schematic partial representation of a pair of scissors having an electrically heated cutter in accordance with the present invention;

FIG. 2 is an enlarged partial cross sectional view in the plane II—II indicated in FIG. 1 of one blade of the scissors incorporating an electrical heating element;

FIG. 3 is an enlarged partial cross sectional view in the plane III—III indicated in FIG. 1;

FIG. 5 is a schematic perspective view of a complete apparatus;

FIG. 9 is a schematic partial perspective view of a razor with a heated blade;

FIG. 10 is an illustrative view of a comb-razor with electrically heated cutters.

BEST AND VARIOUS MODES FOR CARRYING OUT INVENTION

Figure 4:
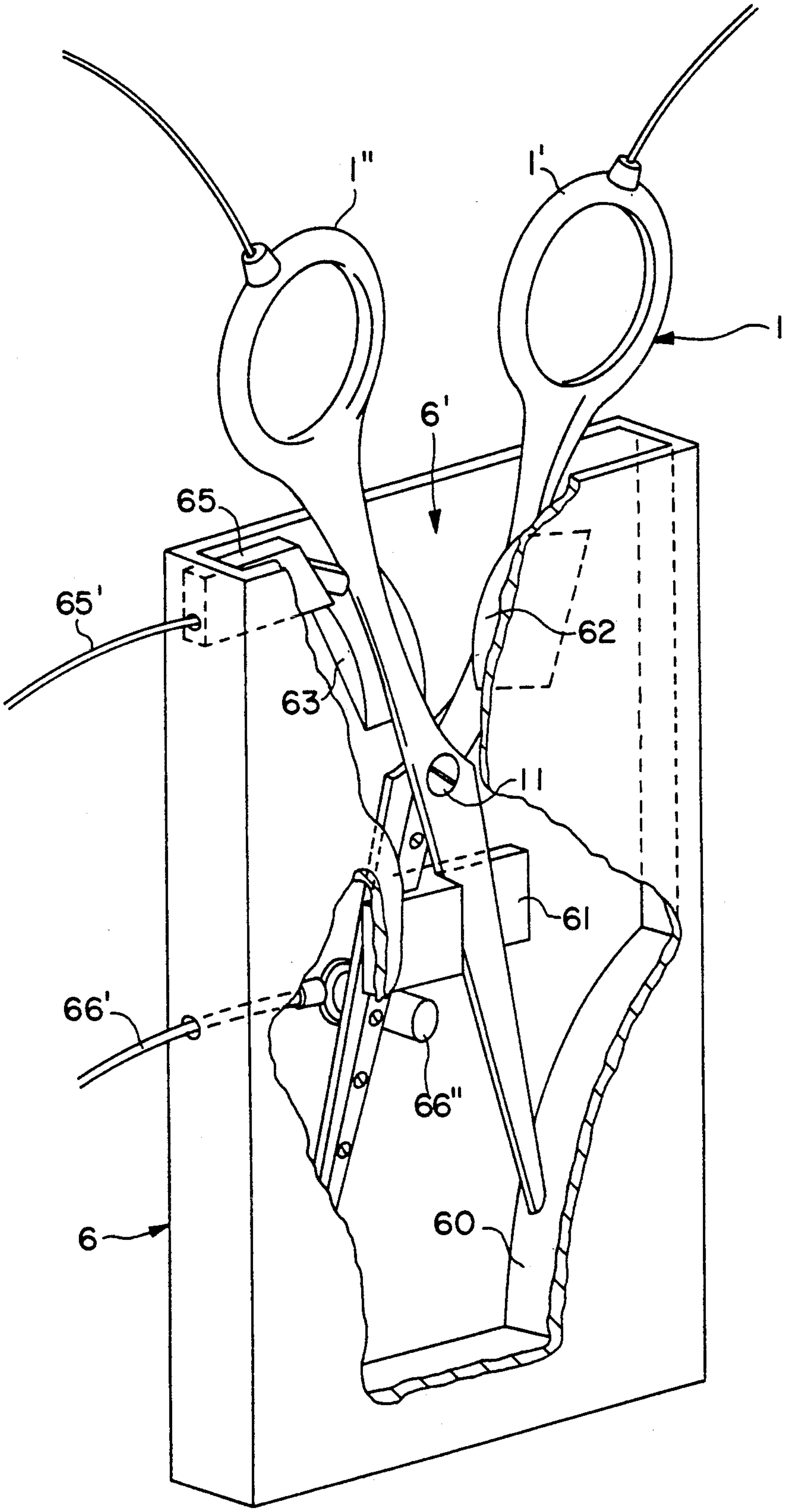
FIG. 4 is a schematic perspective view of a stand-by receptacle for the electrically heated scissors of FIG. 1, equipped with a temperature sensor for controlling the heating of the scissors during stand-by periods.

With reference to FIGS. 1 to 5, a pair of scissors 1 conventionally comprises two blades 1' and 1", pivoted together by means of a screw pivot 11.

According to the present invention, at least one blade or knife of the scissors is heated, at least in correspondence of a cutter piece 10. The cutter 10 is preferably replaceable and may be fixed to respective the blade holder, knife body 1" of the scissors by means of several screws 14. The knife 1" has a recessed portion wherein a flat strip heating resistor 2 is disposed, preferably by interposing a layer of thermally insulating material 22 having a suitably "L"-shaped cross section, in order to reduce heat dispersion through the knife 1" of the scissors and to minimize the power which is necessary for heating the cutter 10 having a sharpened cutting edge 10'.

The heads of the screws 14 for fastening the cutter are received into purposely stepped holes 13 formed through the cutter piece 10, which holes are preferably made with a certain clearance in order to create a space which may be filled with a thermally insulating paste 134, when mounting the cutter. The sleeve of thermally insulating cement 134 will avoid the formation of thermally conductive "bridges" through the assembling screws 14.

The heating resistor 2 is powered through two conductors 20 and 20' which may be laid into a purposely created channel, cut in the handle portion of the scissors, and the electrically insulated conductors 20 and 20' may be permanently set in the channel by means of a potting compound.

An insulated, two-conductor, power-supply cable departs from the handle portion of the scissors and, in the case that both blades of the scissors are electrically heated, the two pairs of conductors emerging from each handle portion of the two knives of the scissors may be electrically connected together in parallel or in electrical series and through a single power-supply cable 21 provided with an end plug 22, the heating resistances may be powered by connecting the plug 22 into an output socket of a power supply 5 which may comprise, as shown, a transformer 5' and an electronic circuitry with an adjusting potentiometer 55, for providing an appropriate power supply in order to attain the desired temperature which may be programmed by means of the knob 55', and controlled by a temperature sensing system 66-66'-66" during stand-by periods. In FIGS. 4 and 5 is also depicted a stand-by scissors holder 6 in the form of a receptacle into which the scissors may be inserted during pauses of the hair cutting work. The scissors holder 6 has a top opening 6' and is provided inside with scissors rests 60, 61, 62 and 63, with a thermostat 66" and with a microswitch 65 for confirming to the control circuit the insertion of the scissors in the stand-by holder. As shown in FIG. 5, the microswitch is connected to the power supply through the cable 65' and the thermostate 66" is connected by the cable 66' to a temperature controlling switch 66. According to this embodiment, the user adjusts the desired temperature of the cutters of the scissors by setting the knob 55'. After the scissors have attained the desired temperature, which is normally comprised between 150° C. and 350° C., preferably between 180° C. and 230° C., the scissors may be used for cutting hair which is desirably cauterized by the contact with the heated cutters of the scissors. During stand-by periods, the scissors may be placed in the holder 6 and by means of the presence confirmation given by the microswitch 65, the temperature of the scissors becomes thermostatically controlled and the control switch 66 provides to interrupt the power supply to the heating resistances when the temperature sensed by the thermostat 66" becomes higher than a preset value. This prevents overheating during stand-by periods and has a power saving function.

According to a preferred embodiment of the invention, a pair of scissors has both cutters heated by heating resistances set in the cutter holding portion of both knives of the scissors in order to promote a most effective cauterizing action during the cutting of hair, and the scissors are also provided with a thermocouple or similar temperature sensor set near at least one of the heated cutters in order to implement a precise and constant temperature control through an appropriate electronic circuitry. Moreover according to such a preferred embodiment, the cable connection between the scissors and the temperature controlled power supply unit is advantageously made by means of a single cable connection through only one of the two handle portions of the scissors. This permits a freer use of the scissors without the hindrance which is inevitably created by having electric cable connections departing from both handle portions of the scissors.

The problem of providing the necessary electric current path through the two heating resistances set in the two pivoted blade portions of the scissors, has been successfully resolved by exploiting the pivoting screw of the scissors as part of the electric path and by utilizing the metal bodies of the scissors also as part of the electric path.

Figure 6:
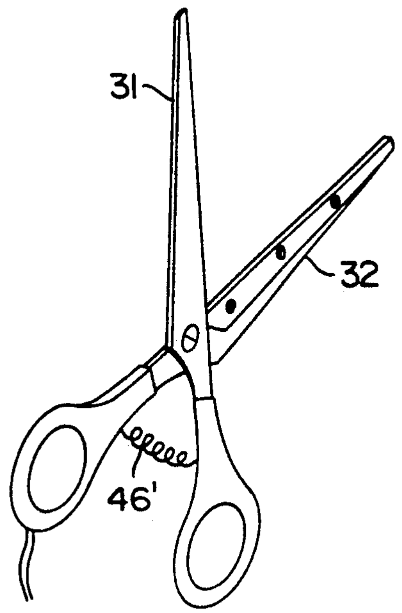
FIG. 6 is a view of a pair of scissors with heated blades according to a further embodiment of the present invention.
Figure 7:
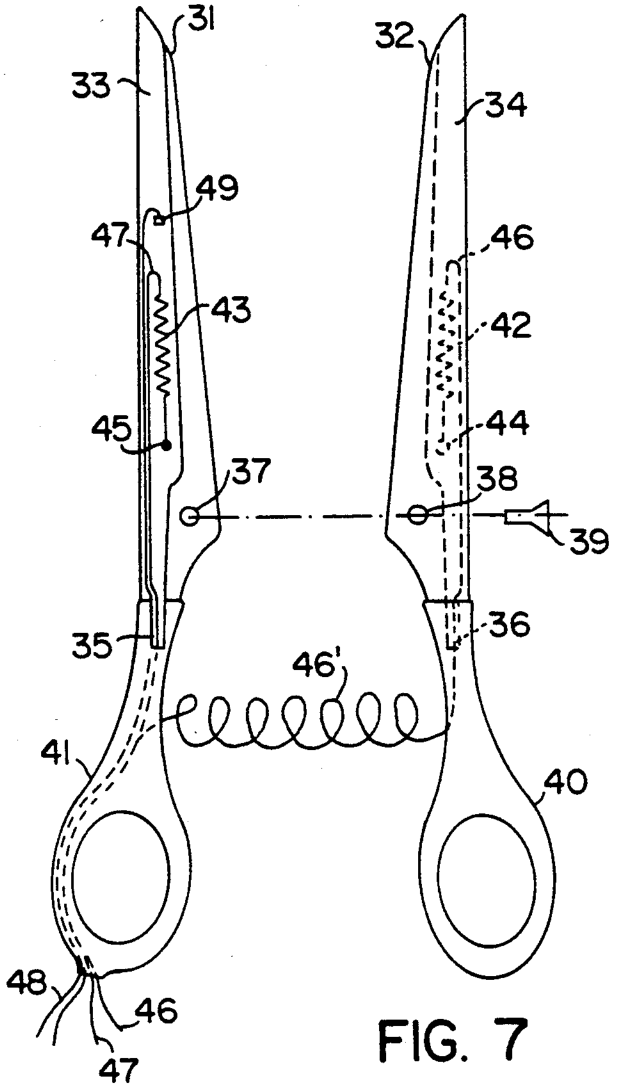
FIG. 7 is a schematic representation of the heated scissors of FIG. 6.
Figure 8:
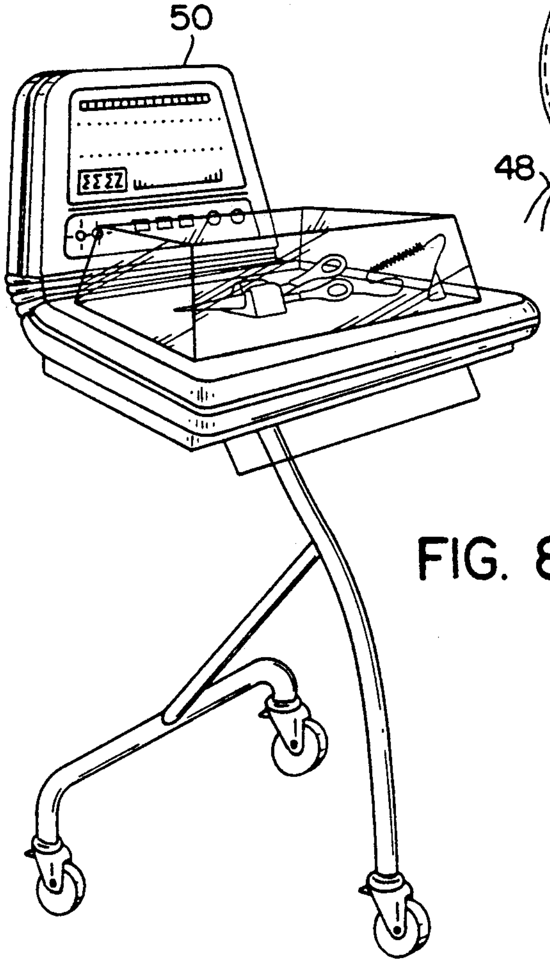
FIG. 8 is a perspective view of a caddie-mounted apparatus of the invention.

The scissors made in accordance with this preferred embodiment are shown in FIGS. 6, 7 and 8. As schematically shown in FIG. 7, the scissors comprise two similar metallic blade holding portions 31 and 32, having a recess, 33 and 34, respectively on their opposing faces. The metallic blade-holding portions have a tail shaped termination, 35 and 36, respectively, and a hole 37, 38 for a pivot screw 39, respectively. Customarily the hole 37 of the blade holder 31 is threaded while the hole 38 of the blade holder 32 has a diameter of a sufficient clearance for a pivot screw 39 to pass through.

The handle portions 40, 41 of both knives of the scissors, are made of a moldable plastic material having a low heat conductivity and are permanently joined to the metallic blade-holding portions 31 and 32; the joint being reinforced by the tail terminations 35 and 36.

Within the recesses 33 and 34 are installed the heating resistances 42 and 43. Each resistance has one end soldered or otherwise electrically connected to the respective metallic blade holder body, respectively at 44 and 45. Each resistance is connected at its other end to an insulated conductor, 46 and 47, respectively. These insulated wires permit the connection of the heating elements to the power supply outlet. In the left hand knife of the scissors, the insulated wire 47 runs along the recess 33, housing the resistance 43, and passes through the conduit purposely formed in the molded plastic handle portion 41 to emerge through a hole at the end of the handle portion. The insulated wire 46 of the other knife of the scissors runs into the recess 34, housing the resistance 42, and passes through a conduit purposely formed in the molded plastic handle portion 40 and emerges through a hole in a neck portion of the handle. The insulated conductor forms several helicoidal turns before entering through a hole in the neck portion of the opposite handle portion of the scissors and passing through a channel purposely formed within the molded plastic body to emerge, together with the other isolated wire 47, through the same hole of the handle portion of the left hand knife of the scissors.

A two-conductor, insulated cable 48 is similarly passed through the same channel of the plastic portion and disposed in the recess 33 and the two conductors terminate with a thermocouple junction 49 which is suitably disposed as near as possible to the respective heated cutter of the scissors. The electric current path through the heating resistors 42 and 43 comprise the metallic body of both blade holder portions of the scissors, electrically connected together by the conducting pivoting pin 39 and the looped portion 46' of the insulated wire 46. In this way the electric circuit is closed while having a cable connection to only one of the two handle portions of the scissors. This arrangement gives a greater freedom to the user of the scissors by eliminating the hindrance represented by having cables departing from both handle portions. The assembled scissors are depicted in FIG. 6. The bridging looped portion 46' is conveniently made with a single isolated wire of a particularly elastic material and does not hinder the use of the scissors.

The use of a thermocouple 49, capable of sensing the exact temperature of the cutters of the scissors, permits the implementation of a constant precise temperature control by means of an electronic circuitry. In this way the power supply to the heating resistances may be automatically modulated so as to maintain a predefined constant temperature of the cutters in any condition of use and of stand-by of the scissors.

The electronic control and power supply may be arranged on a wheeled caddie, as shown in FIG. 8, which may be provided with a control panel 50 containing all the controls and displays for regulating and monitoring the temperature of the cutters.

The invention may also be embodied in a form different from the most common scissors. For example, the same cauterizing action on the hair being cut may be effected by means of a razor type instrument as the one depicted in the schematic partial view of FIG. 9. According to this embodiment, a razor blade 51 may be mounted on a special blade holder 52 containing an electric heating element 53 and preferably a temperature sensing thermocouple (not shown in the figure) for controlling the temperature of the blade 51.

FIG. 10 depicts yet another embodiment of the instrument object of the present invention, in the form of a "combrazor" 54. This hair cutting instrument, has heated blades 55 between the teeth of the comb. Also in this case the blades 55 may be heated to the desired temperature by an electric heating element provided within the body of the instrument.

I claim:

1. Scissors for cutting hair and simultaneously cautherizing ends of the hair that are cut, characterized by the fact that the scissors comprise:

two knives, each having a handle portion and a metallic, recessed, blade-holder portion;

a heating resistor set in a recess of said blade-holder portion of each knife;

a replaceable blade, mounted on the blade-holder portion of each knife, the mounted blade covering said recess and being heated by said heating resistor set in said recess;

at least one of said knives having a recess and at least a heat sensor, set in said recess of said at least one of said knives, and capable of sensing the temperature of the blade of said at least one of said knives heated by said heating resistor.

2. The scissors as defined in claim 1, wherein said heating resistors are electrically connected in series with each other through a metallic pivot of the scissors.

3. The scissors as defined in claim 2, further comprising an insulated cable connection for connecting to a temperature controlled power supply console extends out from the handle portion of only one knife of the scissors; and a bridging electric connection arranged between the pivot and the handle portions of the two knives of the scissors for providing an electric current path to the heating resistor of the other knife of the scissors.

4. The scissors as defined in claim 3, wherein said bridging electric connection comprises a spiral wound insulated cable portion capable of stretching and compressing during the use of the scissors.

* * * * *